(12) United States Patent
Yao

(10) Patent No.: US 10,231,322 B2
(45) Date of Patent: Mar. 12, 2019

(54) HOMOLOGOUS DUAL-ENERGY ACCELERATOR AND ACCELERATOR THERAPY DEVICE

(71) Applicant: SUZHOU LINATECH MEDICAL SCIENCE AND TECHNOLOGY CO., LTD., Industry Park Suzhou, Jiangsu (CN)

(72) Inventor: Jonathan Yi Yao, Jiangsu (CN)

(73) Assignee: Suzhou Linatech Medical Science and Technology Co., Ltd., Jiangsu (CN)

( * ) Notice: Subject to any disclaimer, the term of this patent is extended or adjusted under 35 U.S.C. 154(b) by 0 days.

(21) Appl. No.: 15/552,581

(22) PCT Filed: Apr. 14, 2016

(86) PCT No.: PCT/CN2016/079235
§ 371 (c)(1),
(2) Date: Aug. 22, 2017

(87) PCT Pub. No.: WO2017/152470
PCT Pub. Date: Sep. 14, 2017

(65) Prior Publication Data
US 2018/0192505 A1    Jul. 5, 2018

(30) Foreign Application Priority Data

Mar. 7, 2016   (CN) .......................... 2016 1 0128068

(51) Int. Cl.
*H05H 5/00*    (2006.01)
*H05H 5/03*    (2006.01)
(Continued)

(52) U.S. Cl.
CPC ................. *H05H 5/03* (2013.01); *A61N 5/00* (2013.01); *A61N 5/1037* (2013.01);
(Continued)

(58) Field of Classification Search
CPC ............................... H05H 5/03; A61N 5/1037
(Continued)

(56) References Cited

U.S. PATENT DOCUMENTS 5,849,252 A * 12/1998 Wakamoto ............... A61L 2/08
                                                    422/186.04
8,747,624 B2 * 6/2014 Medoff ..................... C10G 3/00
                                                    204/157.15
(Continued)

FOREIGN PATENT DOCUMENTS

CN         3434679 B2    8/2003
CN       101006541 A     7/2007
(Continued)

*Primary Examiner* — Douglas W Owens
*Assistant Examiner* — Syed M Kaiser
(74) *Attorney, Agent, or Firm* — Muncy, Geissler, Olds & Lowe, P.C.

(57) ABSTRACT

The present invention discloses a homologous dual-energy accelerator and a therapy device comprising the homologous accelerator. The homologous dual-energy accelerator comprises an electron emitting device and an accelerating device, wherein the electron emitting device is located at the input end of the accelerating device, and electrons generated by the electron emitting device are emitted from the output end of the accelerating device after being accelerated by the accelerating device; the homologous dual-energy accelerator further comprises at least one separation deflection device which is arranged on the output end side of the accelerating device and used for changing the motion trail of partial electrons among the electrons accelerated by the accelerating device. The homologous dual-energy accelerator has the advantages that the inventor discovers that the speeds and energy of all electrons are not completely same after the electrons are accelerated by the accelerating device; the inventor uses the separation deflection device arranged on the output end side of the accelerating device through the (Continued)

discovery, the motion trail of partial electrons having relatively low energy level among the particles accelerated by the accelerating device is forcibly changed, the electrons having different energy levels in a homologous electron beam are separated, and two energy levels of electron beams are thus obtained, wherein the high-energy electron beam continues an original path and is used for radiotherapy, and the other path of low-energy electron beam is used for tracking lesions and detecting the therapeutic effect.

8 Claims, 2 Drawing Sheets

(51) Int. Cl.
    *A61N 5/00*     (2006.01)
    *A61N 5/10*     (2006.01)
    *H05H 9/04*     (2006.01)
    *H05H 7/00*     (2006.01)

(52) U.S. Cl.
    CPC ............ *H05H 9/048* (2013.01); *H05H 9/044* (2013.01); *H05H 2007/002* (2013.01); *H05H 2277/11* (2013.01)

(58) Field of Classification Search
    USPC .......................................... 315/506
    See application file for complete search history.

(56) References Cited

U.S. PATENT DOCUMENTS

| | | | |
|---|---|---|---|
| 2005/0092929 A1* | 5/2005 | Schneiker | G21K 1/08 250/396 R |
| 2006/0145088 A1* | 7/2006 | Ma | G21K 1/08 250/396 ML |
| 2006/0255288 A1* | 11/2006 | Petrov | G01N 23/2251 250/398 |
| 2007/0023652 A1* | 2/2007 | Kyushima | H01J 40/14 250/310 |
| 2008/0067406 A1 | 3/2008 | Liu et al. | |
| 2009/0161826 A1* | 6/2009 | Gertner | A61N 5/1017 378/65 |
| 2017/0164910 A1* | 6/2017 | Cao | A61B 6/032 |

FOREIGN PATENT DOCUMENTS

| | | |
|---|---|---|
| CN | 102256434 A | 11/2011 |
| CN | 202160328 U | 3/2012 |
| CN | 103889135 A | 6/2014 |
| CN | 204158405 U | 2/2015 |
| CN | 105072799 A | 11/2015 |
| CN | 205408264 U | 7/2016 |
| CN | 205408264 U | 7/2016 |
| JP | 11111497 A | 4/1999 |
| WO | WO2016/023597 A1 | 2/2016 |

\* cited by examiner

HOMOLOGOUS DUAL-ENERGY ACCELERATOR AND ACCELERATOR THERAPY DEVICE

FIELD OF THE INVENTION

The present invention relates to an accelerator therapy device, and specifically, relates to a homologous dual-energy accelerator and an accelerator therapy device.

BACKGROUND OF THE INVENTION

With the development of tumor radiology and material science, radiotherapy has gradually entered the age of "three precisions" comprising precise positioning, precise planning and precise therapy as an important means for treating cancers. When the rotating plane of a main frame is set to be perpendicular to the horizontal plane, the rotating plane is an X plane, its rotating axis at the moment is defined as a Z axis, the horizontal straight line perpendicular to and cross with the Z axis is an X axis, and the straight line perpendicular to and cross with the Z axis and the X axis respectively is a Y axis. The Z axis and the Y axis define a Y plane, the Y axis and the X axis define an X plane, and the Z axis and the X axis define a horizontal plane (Z plane). The present medical linear accelerator (radiotherapy equipment) is driven by rotation of the main frame to rotate in the X plane or a plane parallel to the X plane, the accelerator follows the main frame to rotate, and the central axis of rays emitted by the accelerator is perpendicular to the rotating axis of the main frame and is intersected with the rotating axis at a point, i.e., an isocenter. Generally, during therapy, the lesion of a patient is put at the isocenter, the main frame is rotated, the accelerator rotates around the lesion in the X plane or the plane parallel to the X plane, and thus rays irradiate the lesion from different directions to better kill sick cells.

Generally, because the position of the lesion is changed with respiration of the patient and the therapeutic condition needs to be known in time, the lesion needs to be positioned before therapy and tracked and detected during therapy. In the past, the patients need to lie on different devices, e.g., the lesion is detected and positioned on an accelerator device having low energy level, then treated on an accelerator device having high energy level, and finally detected on the accelerator device having low energy level to observe the therapeutic effect. In order to solve the problems of low efficiency, poor detection timeliness and the like of said technical solution, two technical solutions have been disclosed at present: I, a homologous dual-beam solution, e.g., Publication No. CN104188679A, the invention relates to a homologous dual-beam medical accelerator, comprising an electron gun, wherein the electron gun is connected with an accelerating tube, the accelerating tube is connected with a coupler, the coupler is connected with a waveguide through a waveguide window, the waveguide is connected with a microwave power source, the microwave power source is connected with a modulator, three energy switches are arranged on the accelerating tube, the three energy switches are respectively located among three accelerating cavities in the accelerating tube, each energy switch comprises an edge coupling cavity and a detuning rod located in the edge coupling cavity, and a movable target is arranged at the outlet end of the accelerator; by controlling the output power of the microwave power source through the modulator and simultaneously adjusting the lengths of the three detuning rods in the edge coupling cavities, energy obtained by electrons emitted by the electron gun in the accelerating tube is adjusted, KeV-level rays and MeV-level rays are thereby obtained, the homologous coaxiality of imaging and therapy is guaranteed, and the healing effect on patients is improved. However, in this solution, the accelerating tube control system is substantially complex, poor in stability and difficult in commercial application. II, a dual-source system, i.e., a KV-level accelerator is integrated to the existing MV-level accelerator system, so that the system simultaneously has two different levels of rays, but also has the problems of high manufacturing cost, heavy structure and the like.

SUMMARY OF THE INVENTION

To solve the above problems, the present invention is aimed at providing a homologous dual-energy accelerator which is simple in structure and reliable and an accelerator therapy device.

To fulfill the above aim, the present invention adopts the following technical solution: a homologous dual-energy accelerator, comprising an electron emitting device and an accelerating device, wherein the electron emitting device is located at the input end of the accelerating device, and electrons generated by the electron emitting device are emitted from the output end of the accelerating device after being accelerated by the accelerating device; the homologous dual-energy accelerator further comprises at least one separation deflection device which is arranged on the output end side of the accelerating device and used for changing the motion trail of partial electrons among the electrons accelerated by the accelerating device.

The homologous dual-energy accelerator has the advantages that the inventor discovers that the speeds and energy of all electrons are not completely same after the electrons are accelerated by the accelerating device; the inventor uses the separation deflection device arranged on the output end side of the accelerating device through the discovery, the motion trail of partial electrons having relatively low energy level among the particles accelerated by the accelerating device is forcibly changed, the electrons having different energy levels in a homologous electron beam are separated, and two energy levels of electron beams are thus obtained, wherein the high-energy electron beam continues an original path and is used for radiotherapy, and the other path of low-energy electron beam is used for tracking lesions and detecting the therapeutic effect.

Further, the separation deflection device comprises:
at least one group of separation deflection coil assembly, arranged on the outlet side of the accelerating device, and used for deflecting the motion direction of part of electrons among the electrons emitted from the accelerating device; and
at least one group of deflection coil assembly, arranged on the motion path of electrons deflected from the motion trail by the separation deflection coil assembly, so that the motion trail of the electrons is deflected again.

Further, the homologous dual-energy accelerator is also provided with a high-energy target and a low-energy target, wherein the high-energy target is arranged on the motion path of electrons having a motion trail not changed, and the low-energy target is arranged on the motion path of electrons having a motion trail changed.

Further, the homologous dual-energy accelerator is also provided with a switching control device which comprises a low-energy switching device and a high-energy switching device; or only the high-energy switching device is configured;

the low-energy switching device is used for controlling whether low energy is output; and the high-energy switching device is used for controlling whether high energy is output.

Further, the high-energy switching device is a high-energy shutter system which can block the electron beam emitted by the electron emitting device from passing or allow the electron beam to pass by opening the through-holes.

Further, the low-energy switching device is a low-energy shutter system which can block the low-energy electron beam separated by the separation deflection device from passing or allow the low-energy electron beam to pass by opening the through-holes.

Further, the low-energy switching device is an electronic switch, the electronic switch is connected with the separation deflection device, and whether the low-energy electron beam is output is controlled by controlling the intensity of the magnetic field of the separation deflection device or on-off of power.

Further, the distance between the motion trail of electrons deflected by the deflection coil assembly and the motion trail of electrons not deflected from the original motion trail is not more than 2 cm.

The present invention further provides an accelerator therapy device, comprising a therapy control device, a main frame and the aforesaid homologous dual-energy accelerator.

Figure 1:
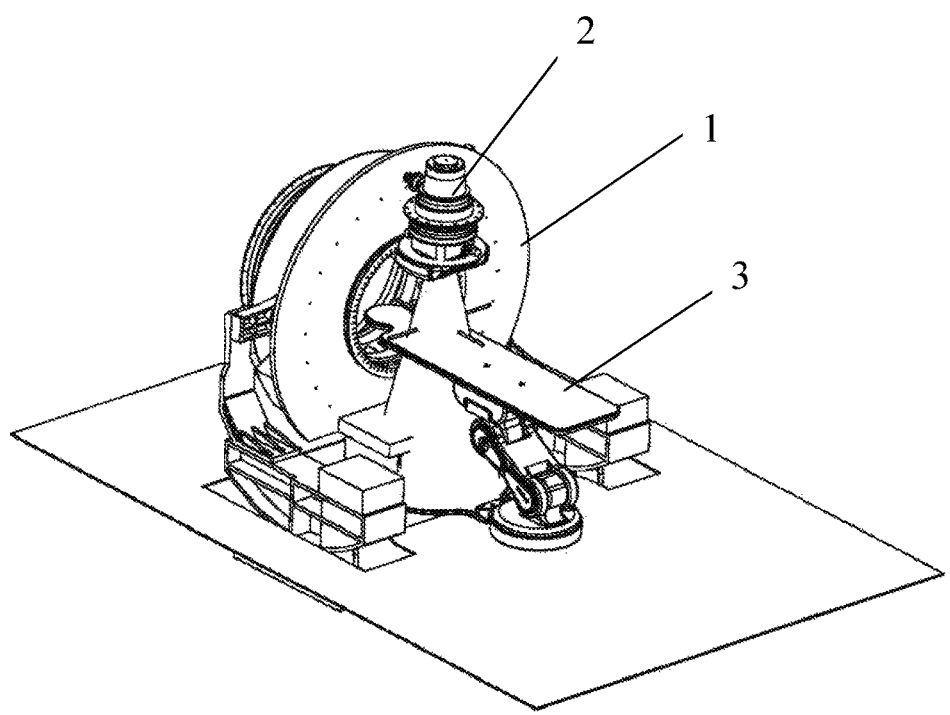
FIGS. 1 and 2 are schematic diagrams of the present invention.

Numbers and letters in the drawings express corresponding components.

1, main frame; 2, dual-energy accelerator; 3, therapy bed; 21, electron emitting device; 22, accelerator; 23, separation deflection device; 231, separation deflection coil assembly; 232, deflection coil assembly; 24, high-energy electron beam; 25, low-energy electron beam.

DETAILED DESCRIPTION OF THE EMBODIMENTS

The present invention will be further described in detail below in combination with the accompanying drawings and specific embodiments.

Figure 2:
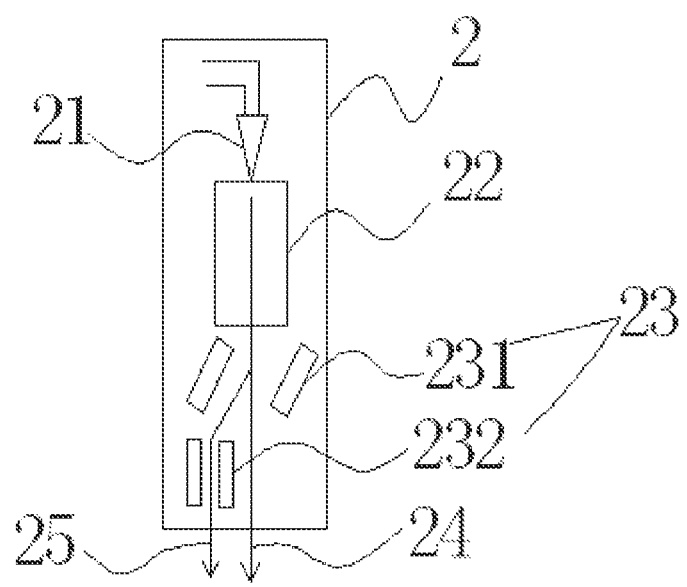

In one embodiment of the present invention, as shown in FIGS. 1 and 2, in order to fulfill the above aim, the present invention adopts the following technical solution:

a homologous dual-energy accelerator 2, comprising an electron emitting device 21 and an accelerating device 22, wherein the electron emitting device 21 is located at the input end of the accelerating device 22, and electrons generated by the electron emitting device 21 are emitted from the output end of the accelerating device 22 after being accelerated by the accelerating device 22; the homologous dual-energy accelerator 2 further comprises at least one separation deflection device 23, which is arranged on the output end side of the accelerating device 22 and used for changing the motion trail of partial electrons among the electrons accelerated by the accelerating device 22.

The homologous dual-energy accelerator has the advantages that the inventor discovers that the speeds and energy of all electrons are not completely same after the electrons are accelerated by the accelerating device; the inventor uses the separation deflection device 23 arranged on the output end side of the accelerating device 22 by using the discovery, the motion trail of partial electrons (low-energy electron beam 25) having relatively low energy level among the particles accelerated by the accelerating device 22 is forcibly changed, the electrons having different energy levels in a homologous electron beam are separated, and two energy levels of electron beams are thus obtained, wherein the high-energy electron beam 24 continues an original path and is used for radiotherapy, and the other path of low-energy electron beam 25 is used for tracking lesions and/or detecting the therapeutic effect.

In practical application, the separation deflection device 23 can complete deflection of the low-energy electron beam by using electromagnetic deflection coils, and comprises: at least one group of separation deflection coil assembly 231, arranged on the outlet side of the accelerating device 22, and used for deflecting the motion direction of part of electrons among the electrons emitted from the accelerating device 22; and at least one group of deflection coil assembly 232, arranged on the motion path of electrons deflected from the motion trail by the separation deflection coil assembly 231, so that the motion trail of the electrons is deflected again.

Generally, the homologous dual-energy accelerator is also provided with a high-energy target and a low-energy target, the high-energy target is arranged on the motion path of electrons having a motion trail not changed, and the low-energy target is arranged on the motion path of electrons having a motion trail changed.

In order to further control electron beams, the homologous dual-energy accelerator is also provided with a switching control device, which comprises a low-energy switching device and a high-energy switching device; or only the high-energy switching device is configured; the low-energy switching device is used for controlling whether low energy is output; and the high-energy switching device is used for controlling whether high energy is output.

The meaning of output is, as for an application side, whether electron beams arrive at a target or the body of patient.

In some embodiments, the high-energy switching device is a high-energy shutter system which can block the electron beam emitted by the electron emitting device 21 from passing or allow the electron beam to pass by opening the through-holes.

In some embodiments, the low-energy switching device is a low-energy shutter system which can block the low-energy electron beam separated by the separation deflection device from passing or allow the low-energy electron beam to pass by opening the through-holes.

In some other embodiments, the low-energy switching device may also be an electronic switch, the electronic switch is connected with the separation deflection device, and whether the low-energy electron beam is output is controlled by controlling the intensity of the magnetic field of the separation deflection device or on-off of power. The separation deflection device stops working by cutting the power for it, or the trail of the low-energy electron beam cannot be changed by reducing the intensity of its magnetic field, which is thus equivalent to stopping output of the special low-energy electron beam. In this case, whether the low-energy electron beam is separately used for working can be conveniently controlled.

In order to facilitate therapy and verification, the distance between the motion trail of electrons deflected by the deflection coil assembly and the motion trail of electrons not deflected from the original motion trail is not more than 2 cm.

The present invention further provides an accelerator therapy device, comprising a therapy control device, a main frame and the aforesaid homologous dual-energy accelerator.

Described above are merely preferred embodiments of the present invention. It should be pointed out that many modifications and improvements can also be made for those of ordinary skill in the art without departing from the concept of the present invention. These modifications and improvements shall fall into the protection scope of the present invention.

The invention claimed is:

1. A homologous dual-energy accelerator, comprising an electron emitting device and an accelerating device, wherein the electron emitting device is located at the input end of the accelerating device, and electrons generated by the electron emitting device are emitted from the output end of the accelerating device after being accelerated by the accelerating device; the homologous dual-energy accelerator further comprises at least one separation deflection device which is arranged on the output end side of the accelerating device and used for changing the motion trail of partial electrons among the electrons accelerated by the accelerating device;

wherein the separation deflection device comprises:
at least one group of separation deflection coil assembly, arranged on the outlet side of the accelerating device, and used for deflecting the motion direction of part of electrons among the electrons emitted from the accelerating device; and
at least one group of deflection coil assembly, arranged on the motion path of electrons deflected from the motion trail by the separation deflection coil assembly, so that the motion trail of the electrons is deflected again;
wherein the motion trail of electrons deflected by the deflection coil assembly is parallel to that of electrons not deflected from the original motion trail.

2. The homologous dual-energy accelerator according to claim 1, wherein the homologous dual-energy accelerator is also provided with a high-energy target and a low-energy target, the high-energy target is arranged on the motion path of electrons having a motion trail not changed, and the low-energy target is arranged on the motion path of electrons having a motion trail changed.

3. The homologous dual-energy accelerator according to claim 1, wherein the homologous dual-energy accelerator is also provided with a switching control device which comprises a low-energy switching device and a high-energy switching device; or only the high-energy switching device is configured;
the low-energy switching device is used for controlling whether low energy is output; and
the high-energy switching device is used for controlling whether high energy is output.

4. The homologous dual-energy accelerator according to claim 3, wherein the high-energy switching device is a high-energy shutter system which can block the electron beam emitted by the electron emitting device from passing or allow the electron beam to pass by opening the through-holes.

5. The homologous dual-energy accelerator according to claim 3, wherein the low-energy switching device is a low-energy shutter system which can block the low-energy electron beam separated by the separation deflection device from passing or allow the low-energy electron beam to pass by opening the through-holes.

6. The homologous dual-energy accelerator according to claim 3, wherein the low-energy switching device is an electronic switch, the electronic switch is connected with the separation deflection device, and whether the low-energy electron beam is output is controlled by controlling the intensity of the magnetic field of the separation deflection device or on-off of power.

7. The homologous dual-energy accelerator according to claim 1, wherein the distance between the motion trail of electrons deflected by the deflection coil assembly and the motion trail of electrons not deflected from the original motion trail is not more than 2 cm.

8. An accelerator therapy device, comprising a therapy control device, a main frame and the homologous dual-energy accelerator of claim 1.

* * * * *